(12) United States Patent
Keal

(10) Patent No.: US 8,843,345 B2
(45) Date of Patent: Sep. 23, 2014

(54) MOTION DETERMINATION

(75) Inventor: William Kerry Keal, Santa Clara, CA (US)

(73) Assignee: Invensense, Inc., San Jose, CA (US)

(*) Notice: Subject to any disclaimer, the term of this patent is extended or adjusted under 35 U.S.C. 154(b) by 422 days.

(21) Appl. No.: 13/164,136

(22) Filed: Jun. 20, 2011

(65) Prior Publication Data

US 2012/0323520 A1 Dec. 20, 2012

(51) Int. Cl.
| | |
|---|---|
| G01P 15/00 | (2006.01) |
| G01C 17/00 | (2006.01) |
| G01C 19/00 | (2013.01) |
| G06F 15/00 | (2006.01) |
| G01C 19/5776 | (2012.01) |

(52) U.S. Cl.
CPC .................... G01C 19/5776 (2013.01)
USPC ............ 702/141; 702/147; 702/150; 702/189

(58) Field of Classification Search
USPC ................. 702/141, 189, 150; 73/1.79, 503.3
See application file for complete search history.

(56) References Cited

U.S. PATENT DOCUMENTS

| 5,323,337 A * | 6/1994 | Wilson et al. ................ 702/73 |
| 6,758,080 B1 | 7/2004 | Ragan et al. |
| 2003/0036847 A1* | 2/2003 | Geier et al. .................. 701/209 |
| 2004/0168797 A1* | 9/2004 | Barrow ...................... 166/255.1 |
| 2005/0251328 A1 | 11/2005 | Merwe et al. |
| 2005/0283988 A1 | 12/2005 | Sato et al. |
| 2006/0229869 A1* | 10/2006 | Nemer ........................ 704/226 |
| 2008/0262728 A1* | 10/2008 | Lokshin et al. ............... 701/216 |
| 2009/0007661 A1* | 1/2009 | Nasiri et al. ............... 73/504.03 |
| 2010/0292943 A1 | 11/2010 | Minor et al. |

FOREIGN PATENT DOCUMENTS

WO 0055652 A1 9/2000

OTHER PUBLICATIONS

Delaney, "Signal Detection Using Third-Order Moments", 1994, Circuits, Systems and Signal Processing vol. 13, Issue 4, pp. 481-496.*

International Search Report and Written Opinion mailed Aug. 16, 2012 for International Application No. PCT/US 12/35848, 10 pages.

* cited by examiner

Primary Examiner — Michael Nghiem
Assistant Examiner — Alexander Satanovsky
(74) Attorney, Agent, or Firm — Sawyer Law Group, P.C.

(57) ABSTRACT

Described herein are systems and methods that can employ a motion detection algorithm to determine whether a sensor has experienced a motion event or a no motion event. The sensor can be any sensor that can be used to identify and/or characterize motion. Upon receiving a signal from the sensor, moments of the signal can be calculated. Then, the moments can be compared to determine whether the signal is Gaussian. If the signal is a Gaussian signal, the algorithm determines that the signal is due to a no motion event. If the signal is a non-Gaussian signal, the algorithm determines that the signal is due to a motion event.

24 Claims, 14 Drawing Sheets

MOTION DETERMINATION

TECHNICAL FIELD

This disclosure relates generally to determining whether measurements from sensors are due to the sensors being moved.

BACKGROUND

Traditional motion detection systems can observe signals from sensors over a period of time and verify that the signals are within a small range for the period of time. If the signals are within the small range for the period of time, the motion detection systems can determine that a no motion event has occurred. However, this determination that a no motion event has occurred can take a long time (e.g., eight seconds), making the motion detection systems inefficient.

The above-described deficiencies of traditional motion detection systems are merely intended to provide an overview of some of problems of current technology, and are not intended to be exhaustive. Other problems with the state of the art, and corresponding benefits of some of the various non-limiting embodiments described herein, can become further apparent upon review of the following detailed description.

SUMMARY

The following presents a simplified summary of the claimed subject matter in order to provide a basic understanding of some aspects described herein. This summary is not an extensive overview, and is not intended to identify key/critical elements or to delineate the scope of the claimed subject matter. Its sole purpose is to present some concepts in a simplified form as a prelude to the more detailed description that is presented later.

Described herein are systems and methods that can promote a fast and reliable indication of whether a sensor has been moved or is stationary. This determination can be based on an analysis of a signal from the sensor. More specifically, upon receiving the signal from the sensor, moments of the signal can be analyzed to determine whether the signal is Gaussian. The sensor can include any sensor that produces Gaussian noise while not moving or produces a response close to Gaussian noise. Examples of sensors that can be used in connection with this algorithm can include: a gyroscope, an accelerometer, a compass, a pressure sensor, a proximity sensor, a range sensor, or the like. The sensor can be any sensor that can be used to identify and/or characterize motion. The input can also be parameters derived from sensor data such as a quaternion.

If the signal is determined to be non-Gaussian, then the signal is due to the sensor being moved. However, if the signal is determined to be Gaussian, the systems and methods can determine that the sensor has not been moved. If the sensor is a gyroscope, and when the systems or methods determine that the signal is a Gaussian signal, a gyroscope bias can be determined. Additionally, if it is known a priori that the sensor has not been moved, the systems and methods can use the same information to determine whether the sensor is working and/or to determine a quality of noise.

The following description and annexed drawings set forth certain illustrative aspects of the specification. These aspects are indicative, however, of but a few of the various ways in which the principles of the specification can be employed. Other advantages and novel features of the specification will become apparent from the following detailed description of the specification when considered in conjunction with the drawings.

BRIEF DESCRIPTION OF THE DRAWINGS

Non-limiting and non-exhaustive embodiments of the subject disclosure are described with reference to the following figures, wherein like reference numerals refer to like parts throughout the various views unless otherwise specified.

DETAILED DESCRIPTION

Various non-limiting embodiments of a remote control device and methods utilized with the remote control device are described herein. In the following description, numerous specific details are set forth in order to provide a thorough understanding of one or more embodiments. One skilled in the relevant art will recognize, however, that the techniques described herein can be practiced without one or more of the specific details, or with other methods, components, materials, etc., and is not limited by these specific details and examples. In other instances, well-known structures, materials, and/or operations are not shown or described in detail to avoid obscuring certain aspects.

Reference throughout this specification to "one embodiment," or "an embodiment," means that a particular feature, structure, or characteristic described in connection with the embodiment is included in at least one embodiment. Thus, the appearances of the phrase "in one embodiment," or "in an embodiment," in various places throughout this specification are not necessarily all referring to the same embodiment. Furthermore, the particular features, structures, or characteristics can be combined in any suitable manner in one or more embodiments.

The word "exemplary" is used herein to mean serving as an example, instance, or illustration. For the avoidance of doubt, the subject matter disclosed herein is not limited by such examples. Any aspect described herein as "exemplary" is not necessarily to be construed as preferred or advantageous over other, nor is it meant to preclude equivalent exemplary structures and techniques known to those of ordinary skill in the art. Furthermore, to the extent that the terms "includes," "has," "contains," and other similar words are used in either the detailed description or the claims, such terms are intended to be inclusive—in a manner similar to the term "comprising" as an open transition word—without precluding any additional or other elements.

As used in this application, the term "or" is intended to mean an inclusive "or" rather than an exclusive "or." Therefore, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Figure 1:
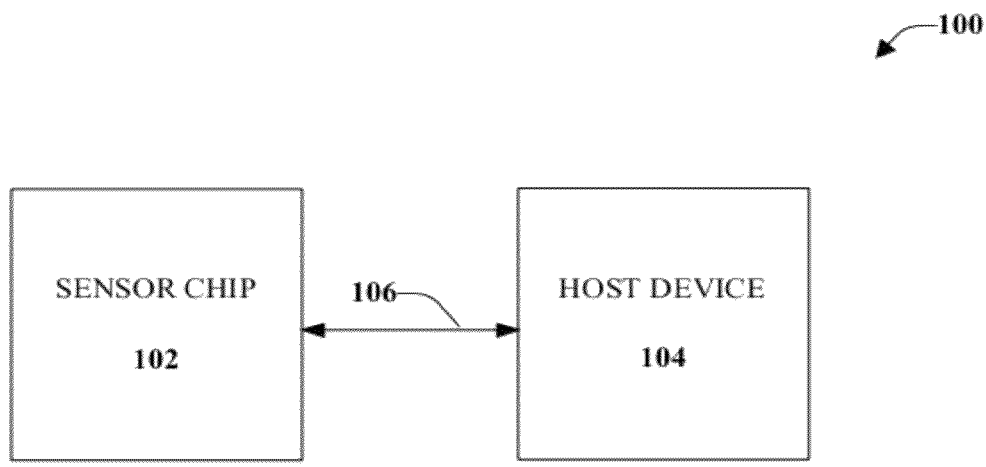
FIG. 1 is a schematic block diagram of a system that determines whether a sensor has experienced a motion event or a no motion event.

Referring now to FIG. 1, illustrated is a schematic block diagram of a system 100 that determines whether a sensor has experienced a motion event or a no motion event. The system 100 can be part of an electronic device (not shown). By way of example and not limitation, the electronic device can be a mobile phone.

The system 100 can include a sensor chip 102. The sensor chip 102 can be, for example, an integrated circuit (IC) chip. The sensor chip 102 can have one or more sensors (e.g., on the IC chip)(not shown). The sensors can be any type of sensor capable of producing a Gaussian signal (e.g., the signal can include data that satisfy a Gaussian relationship). Examples of sensors that can be used in connection with this algorithm can include: a gyroscope, an accelerometer, a compass, a pressure sensor, a proximity sensor, a range sensor, or the like. The sensor can be any sensor that can be used to identify and/or characterize motion. The system can also use parameters derived from sensor data such as a quaternion.

For example, the sensors can be MEMS-based motion sensors. An example of a MEMS-based motion sensor is an accelerometer, which can be used to measure linear acceleration. The physical mechanisms underlying MEMS-based accelerometers include capacitive, piezoresistive, electromagnetic, piezoelectric, ferroelectric, optical and tunneling. MEMS-based accelerometers can be simple devices consisting of a cantilever beam with a predetermined test mass (also known as proof mass seismic mass). Under the influence of external accelerations, the mass deflects from its neutral position. This deflection is measured in an analog or digital manner. Commonly, the capacitance between a set of fixed beams and a set of beams attached to the proof mass is measured.

Other types of MEMS-based accelerometers can contain a small heater at the bottom of a very small dome, which heats the air inside the dome to cause it to rise. A thermocouple on the dome determined where the heated air reaches the dome and the deflection off the center is a measure of the acceleration applied to the sensor. MEMS-based accelerometers generally operate in-plane, that is, they are designed to be sensitive only to a direction of the plane of the die. By integrating two devices perpendicularly on a single die a two-axis accelerometer can be made. By adding an additional out-of-plane device, three axes can be measured. Accelerometers with integral electronics offer readout electronics and self-test capability.

Another example of a MEMS-based motion sensor is a compass, which is an instrument used for determining direction relative to the earth's magnetic pole. A compass can include a magnetized pointer free to align itself with the earth's magnetic field. Miniature compasses are usually built out of two or three magnetic field sensors, for example Hall sensors, that provide data for a microprocessor. The correct heading relative to the compass can be calculated using trigonometry. Often, a miniature compass is a discrete component which outputs either a digital or analog signal proportional to its orientation. This signal can be interpreted by a controller or a microprocessor. The compass can use highly calibrated internal electronics to measure the response of the compass to the earth's magnetic field. Examples of miniature compasses available in the marketplace include the HMC1051Z single-axis and the HMC1052 two-axis magneto-resistive sensors sold by Honeywell International Inc., the AK8973 3-axis electronic compass sold by Asahi Kasei Microdevices Corporation, and the AMI 201 (2-axis) and the AMI 302 (3-axis) electronic compass modules sold by Aichi Micro Intelligent Corporation of Japan.

Another example of a MEMS-based motion sensor is a gyroscope, which is a device used for measuring or maintaining orientation, based on the principles of conservation of angular momentum. MEMS-based gyroscopes use vibrating proof masses. Those masses typically vibrate at a high frequency. As the sensor housing rotates in inertial space a Coriolis force is induced on the proof mass. The Coriolis force causes a vibration in an orthogonal plane and the amplitude of the orthogonal motion can be measured. This type of device is also known as a Coriolis vibratory gyro because as the plane of oscillation is rotated, the response detected by the transducer results from the Coriolis term in its equations of motion ("Coriolis force"). A vibrating structure gyroscope can be implemented as a tuning fork resonator, a vibrating wheel or a wine glass resonator using MEMS technology.

One of ordinary skill in the art will appreciate that the subject innovation is not limited to MEMS based devices, that the MEMS based embodiments disclosed herein are exemplary, and that the subject innovation can be implemented with any sensor that can be incorporated in a handheld device. Examples of sensors that can be used in connection with this algorithm can include: a gyroscope, an accelerometer, a compass, a pressure sensor, a proximity sensor, a range sensor, or the like. The sensor can be any sensor that can be used to identify and/or characterize motion. For example, quartz sensors, can also be used herein. Other types of sensors that include mechanical components on the micron or millimeter scale and can be combined with electronic circuitry can also be used in the subject innovation.

The sensor chip 102 can also have a processing power and/or capability. For example, the sensor chip 102 can have a processor (e.g., on the IC chip). The processor can be communicatively coupled to the sensor, enabling the processor to receive a signal from the sensor. For example, on the sensor chip 102, the processor can be located next to the sensor. This can enable the processor to receive a signal and/or data from the sensor and process the signal and/or data (e.g., according to a motion detection algorithm) to determine whether the signal and/or data is due to a motion event or a no motion event. However, the processing power and/or capability associated with the sensor chip 102 can be limited (e.g., due to size constraints).

To compensate for the limited processing power and/or capability, the sensor chip 102 can be associated with a host device 104 (e.g., a CPU unit of a mobile device). The host device 104 can also have a processing power and/or capability. The processing power and/or capability of the host device 104 can be greater than the processing power and/or capability of the sensor chip 102.

The host device 104 can include a processor (not shown) with a greater processing power than the processor associated with the sensor chip 102. The sensor chip 102 and the host device 104 can be communicatively coupled, for example, through a coupling 106. The coupling can include, for example, an I2C bus and/or a serial port. The sensor chip 102 can send a signal and/or data from the sensors to the host device 104 across the connection 106. The processor of the host device 104 can independently process the signal and/or data (e.g., according to the motion detection algorithm) to determine whether the signal and/or data is due to a motion event or a no motion event.

Both the sensor chip 102 and the host device 104 can independently process signals and/or data from the sensors. Having the sensor chip 102 with a processing power to run, for example, a motion detection algorithm, to detect whether the signal and/or data is due to a motion event or a no motion event can reduce the amount of traffic between the sensor chip 102 and the host device 104 across the connection 106. For example, the host device 104 can receive a signal and/or data from the sensor less frequently than the processor on the sensor chip 102 receives the data.

The following non-limiting example is described to give context for system 100. The sensor chip 102 can include a gyroscope (not illustrated). The gyroscope can send data to the processor associated with the sensor chip 102 and across the connection 106 to the processor associated with the host device 104 (e.g., for parallel processing). The gyroscope can send data to the host device 104 less frequently than it sends data to the processor associated with the sensor chip 102 (e.g., reducing the amount of traffic between the sensor chip 102 and the host device 104). The processor associated with the sensor chip 102 and the processor associated with the host device 104 can independently run a motion detection algorithm to determine if the data is due to a motion event (e.g., a person moving the mobile phone) or a no motion event (e.g., noise).

When the host device 104 determines that the data is due to a no motion event, the host can record a gyroscope bias. The gyroscope bias, for example, can be applied to the gyroscope signal to reduce the error between true rotation rate and measured rotation rate. The gyroscope bias also can be utilized, for example, for temperature compensation. The processor of the sensor device 102 can also determine that the data is due to a no motion event and record a gyroscope bias that can be utilized, for example, for temperature compensation. The processor of the sensor device 102 can utilize the data that is normally sent across the connection 106 (e.g., transport layer) to feed its motion detection algorithm. If the processor associated with the sensor device 102 determines that a no motion event has occurred, and a time period has elapsed and/or a temperature change has occurred, the processor associated with the sensor device 102 can utilize the gyroscope biases it calculated and/or read from the gyroscope to update the gyroscope biases. The processor associated with the host device 104 can have similar functionality. This is an improvement over traditional systems that, for example, ask the gyroscope what the motion state is at certain time periods and read the bias of the gyroscope and the temperature if the bias and the temperature were not being sent to the host device 104.

Additionally, according to another non-limiting example, a gyroscope bias can have a correlation to temperature. When determining the gyroscope bias, the bias and temperature can be saved and sent to a temperature compensation algorithm. Over time, for example, the temperature compensation algorithm can learn the relationship between the gyroscope bias and temperature. This compensation can then be applied to reduce the overall gyroscope error as temperature changes in the figure.

For example, a gyroscope bias algorithm can run on the sensor device 102 (e.g., on hardware of the sensor device 102). A temperature compensation algorithm can, additionally or alternatively, for example, run on the host device 104. The gyroscope bias can be communicated back to the host device 104 to be employed in connection with the temperature compensation algorithm so to facilitate the temperature compensation algorithm learning the temperature and gyroscope bias relationship.

Alternatively, the gyroscope bias algorithm can run on the sensor device 102. The gyroscope bias algorithm can also run on the host device 104. Also running on the host device 104 can be the temperature compensation algorithm. With the gyroscope bias algorithm and the temperature compensation algorithm both running on host device 104, there can be, for example, a reduction in communication between the sensor device 102 and the host device 104 across the coupling 106 (e.g., through I2C or serial ports) because typically gyroscope data is sent to the host device 104 when the gyroscope is active, so additional data, including a no motion message and/or the gyroscope bias, would not have to be sent. Even if the gyroscope bias algorithms running on the sensor device 102 and the host device 104 were different and/or used different data rates, the algorithms could give similar enough results to be useful.

FIGS. 2, 3, 7, 10 and 11 illustrate methods for determining whether a signal from a sensor is due to a motion event or a no motion event and/or motion detection algorithms. For simplicity of explanation, the methodologies are depicted and described as a series of acts. It is to be understood and appreciated that the various embodiments are not limited by the acts illustrated and/or by the order of acts. For example, acts can occur in various orders and/or concurrently, and with other acts not presented or described herein. Furthermore, not all illustrated acts can be required to implement the methodologies in accordance with the disclosed subject matter. In addition, those skilled in the art will understand and appreciate that the methods could alternatively be represented as a series of interrelated states via a state diagram or events. Additionally, it should be further appreciated that the methods described hereafter are capable of being stored on an article of manufacture (e.g., a computer readable storage medium) to facilitate transporting and transferring such methodologies to computers. The term article of manufacture, as used herein, is intended to encompass a computer program accessible from any computer-readable device, carrier, or media. For example, these methods and/or algorithms can be executed by the processor associated with sensor chip 102 and/or the processor associated with host device 104.

Figure 2:
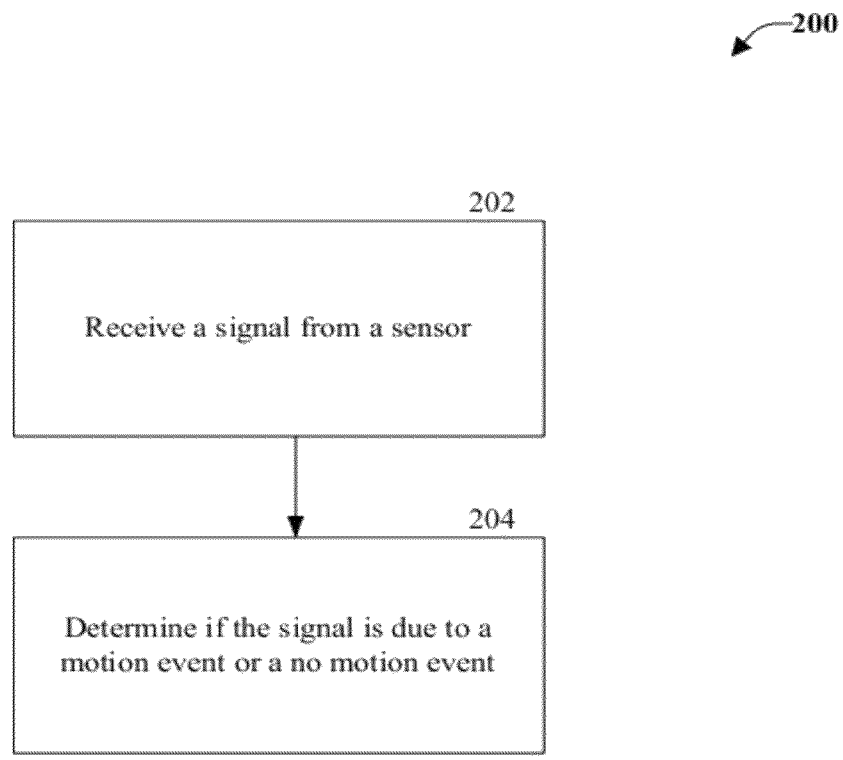
FIG. 2 is a schematic process flow diagram of a method for determining whether a sensor has experienced a motion event or a no motion event.

Referring now to FIG. 2, illustrated is a schematic process flow diagram of a method 200 for determining whether a sensor has experienced a motion event or a no motion event. At element 202, a processor can receive a signal and/or data from a sensor. Examples of sensors that can be used in connection with this algorithm can include: a gyroscope, an accelerometer, a compass, a pressure sensor, a proximity sensor, a range sensor, or the like. The sensor can be any sensor that can be used to identify and/or characterize motion. The data can be, for example, quaternion data. The processor can be associated with a sensor chip (e.g., sensor chip 102 of FIG. 1). The processor associated with the sensor chip can be located next to the sensor (e.g., on an IC chip). The processor can also be associated with a host device (e.g., host device 104 of FIG. 1). The processor associated with the host device can receive the signal and/or data from the sensor across a transport layer (e.g., connection 106 of FIG. 1).

At element 202, the processor (e.g., the processor associated with the sensor chip and/or the processor associated with the host device) can determine if the signal is due to a motion event or a no motion event. The processor associated with the sensor chip and/or the processor associated with the host device can apply an algorithm independently to determine if the signal and/or data are due to a motion event or a no motion event. The processors can employ algorithms described, for example, in FIGS. 3 and/or 7 to determine if the signal and/or data are due to a motion event or a no motion event. These methods can be based the determination of whether the signal and/or data is due to a motion event or a no motion event by analyzing the type of signal and/or data. For example, by analyzing the type of signal and/or data, the signal and/or data can be determined to be a Gaussian process or a non-Gaussian process. If the signal/and or data is determined to be Gaussian, it can be assumed that a no motion event has occurred. In contrast, if the signal and/or data are determined to be non-Gaussian, it can be assumed that a motion event has occurred. In practice, a false motion event is of less concern than a false no motion event, so the algorithms described herein take advantage of this fact. It will be understood that the algorithms described herein can be combined with other motion determination algorithms to further strengthen to no motion event criterion.

Figure 3:
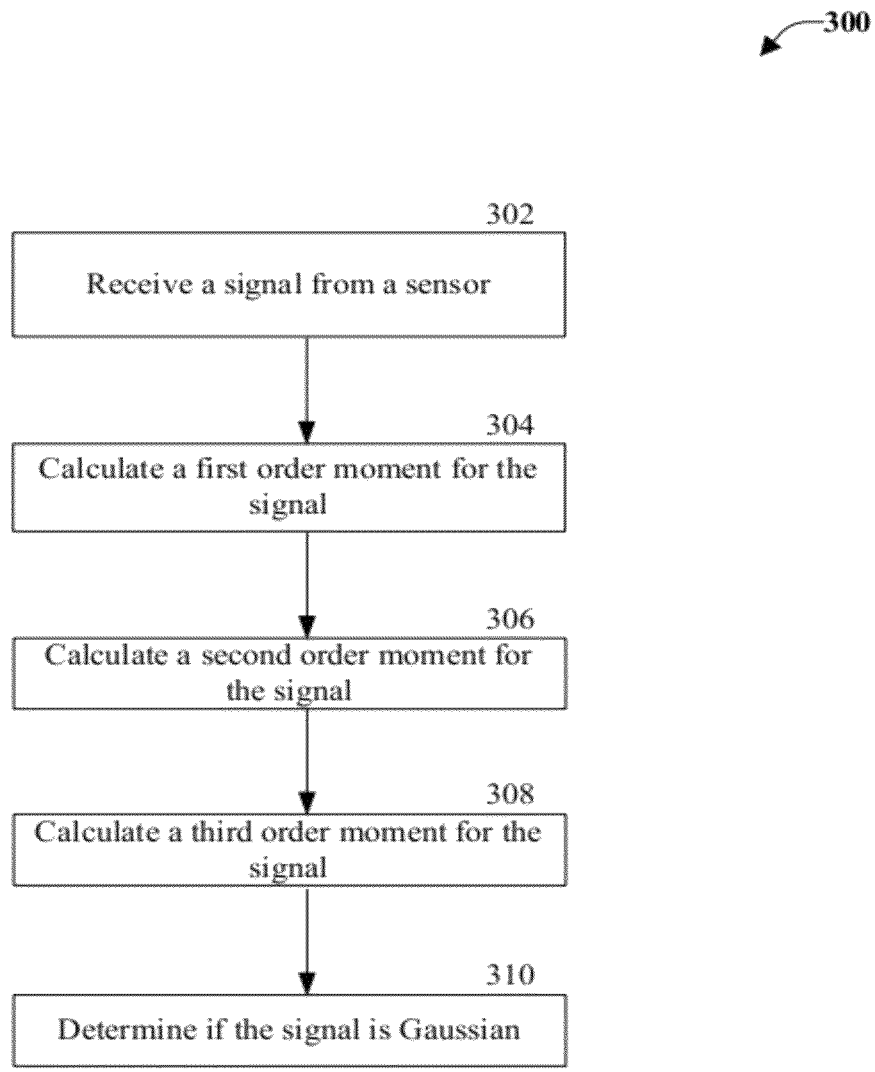
FIG. 3 is a schematic process flow diagram of a method for determining whether a signal is Gaussian.

Referring now to FIG. 3, illustrated is a schematic process flow diagram of a method 300 for determining whether a signal and/or data received from a sensor is Gaussian. As described above, if the signal and/or data are determined to be Gaussian, it can be determined that no motion event has occurred. In contrast, if the signal and/or data are determined to be non-Gaussian, it can be determined that a motion event has occurred.

At element 302, a signal can be received from a sensor (e.g., as described above). The signal can include data of size N. For example, the data can be $[x_0, x_1, \ldots, x_{N-1}]$. Additionally or alternatively, all axes of data from the sensor can be utilized (e.g., three axes). The processor can determine whether the data is Gaussian utilizing estimated moments.

At element 304, the estimated first order moment for the data can be calculated. For example, the estimated first order moment ($T_1$) can be calculated according to the following:

$$T_1 = \frac{1}{N} \sum_{n=0}^{N-1} (x_n)^1,$$ EQUATION 1 where $T_1$ is the first order moment, N is the size of the data, and $x_n$ is a data point within $[x_0, x_1, \ldots, x_{N-1}]$.

At element 306, the estimated second order moment for the data can be calculated. For example, the estimated second order moment ($T_2$) can be calculated according to the following:

$$T_2 = \frac{1}{N} \sum_{n=0}^{N-1} (x_n)^2,$$ EQUATION 2 where $T_2$ is the estimated second order moment, N is the size of the data, and $x_n$ is a data point within $[x_0, x_1, \ldots, x_{N-1}]$.

At element 308, the estimated third order moment for the data can be calculated. For example, the estimated third order moment ($T_3$) can be calculated according to the following:

$$T_3 = \frac{1}{N} \sum_{n=0}^{N-1} (x_n)^3,$$ EQUATION 3 where $T_3$ is the estimated third order moment, N is the size of the data, and $x_n$ is a data point within $[x_0, x_1, \ldots, x_{N-1}]$.

It is well known, that if a process is Gaussian, all third order and higher moments can be calculated from the first order moment and the second order moment. At element 310, it can be determined if the signal is Gaussian by comparing the estimated third order moment calculated according to EQUATION 3 ($T_3$) to a theoretical third order moment. The theoretical third order moment can be calculated based on the estimated first order moment ($T_1$) and the estimated second order moment ($T_2$). A difference ($V_3$) between the estimated third order moment ($T_3$) and the theoretical third order moment can be expressed as:

$$V_3 = T_3 - 3*T_2*T_1 + 2*T_1^3$$ EQUATION 4, where $V_3$ is the difference between the estimated third order moment ($T_3$) and the theoretical third order moment based on $T_1$ and $T_2$, $T_1$ is the estimated first order moment and $T_2$ is the estimated second order moment.

In a Gaussian process, the third order moment $T_3$ should be equal to the moment computed by using the true first and second order moments. By using estimates of the moments and comparing the relationship when using estimates, the errors produced on the comparison should be small for a Gaussian process. For example, the absolute value of $V_3$ should be within a threshold range for the process to be Gaussian. Therefore, if the absolute value of $V_3$ is less than the threshold, the process is determined to be Gaussian, and the data from the sensor is determined to be due to a no motion event. In contrast, if the absolute value of $V_3$ is greater than the threshold, the process is determined to be non-Gaussian, and the data from the sensor is determined to be due to a motion event. The threshold may have to be increased if the sensor noise is not strictly Gaussian.

Figure 4:
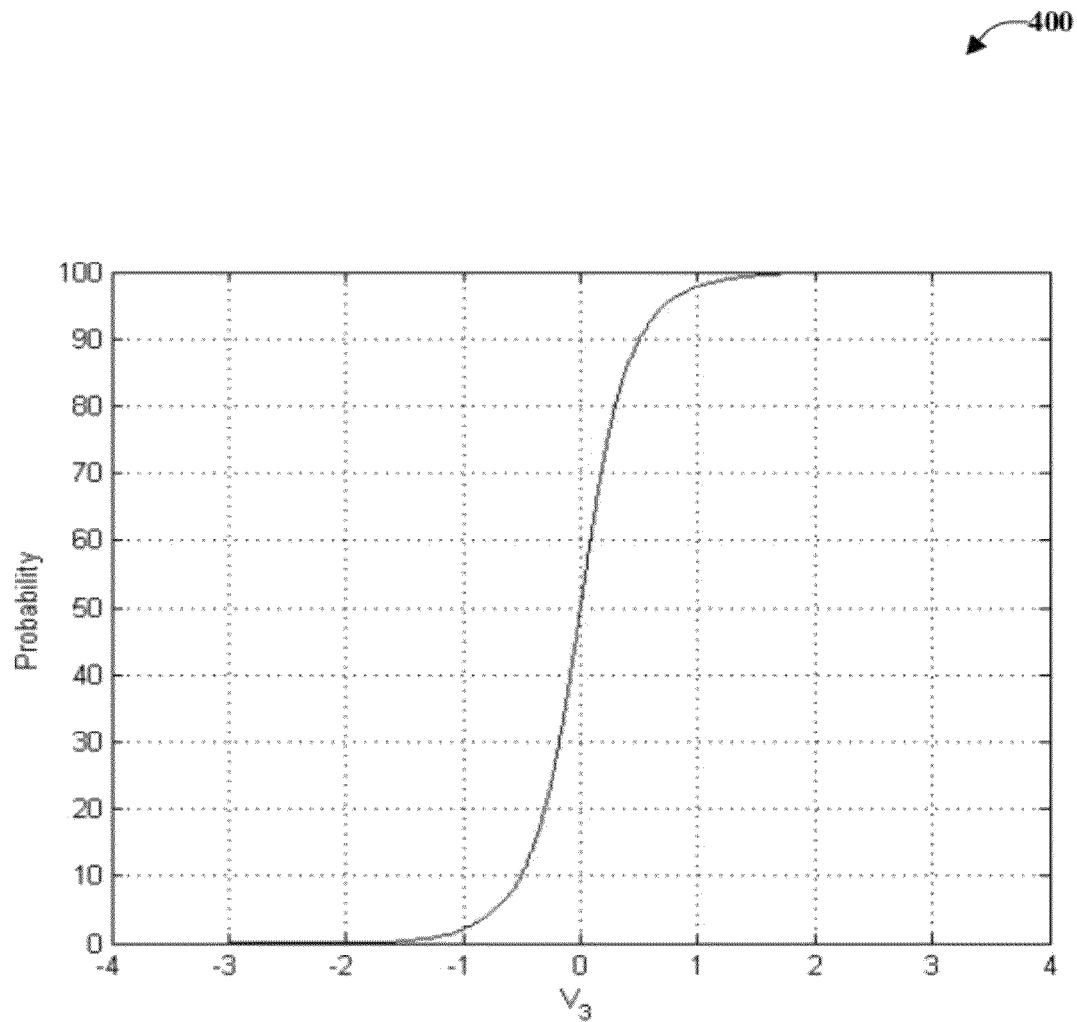
FIG. 4 is a plot of a cumulative probability function for the difference between an estimated third order moment and a theoretical third order moment ($V_3$) with twenty-five samples and a standard deviation of one.

$V_3$ can be computed according to EQUATION 4 for a known Gaussian sequence (e.g., $[x_1, x_2, \ldots, x_{N-1}]$ is known to be Gaussian) with a standard deviation of 1. Referring now to FIG. 4, illustrated is a plot 400 of a cumulative probability function for $V_3$ with twenty-five samples (N=25) and a standard deviation of 1. Given the plot 400, a probability of getting a no motion event can be set and a range that $V_3$ needs to be within to achieve the probability. For example, for a probability of eighty percent, $V_3$ must be within a threshold of about −0.5 and 0.5.

Figure 5:
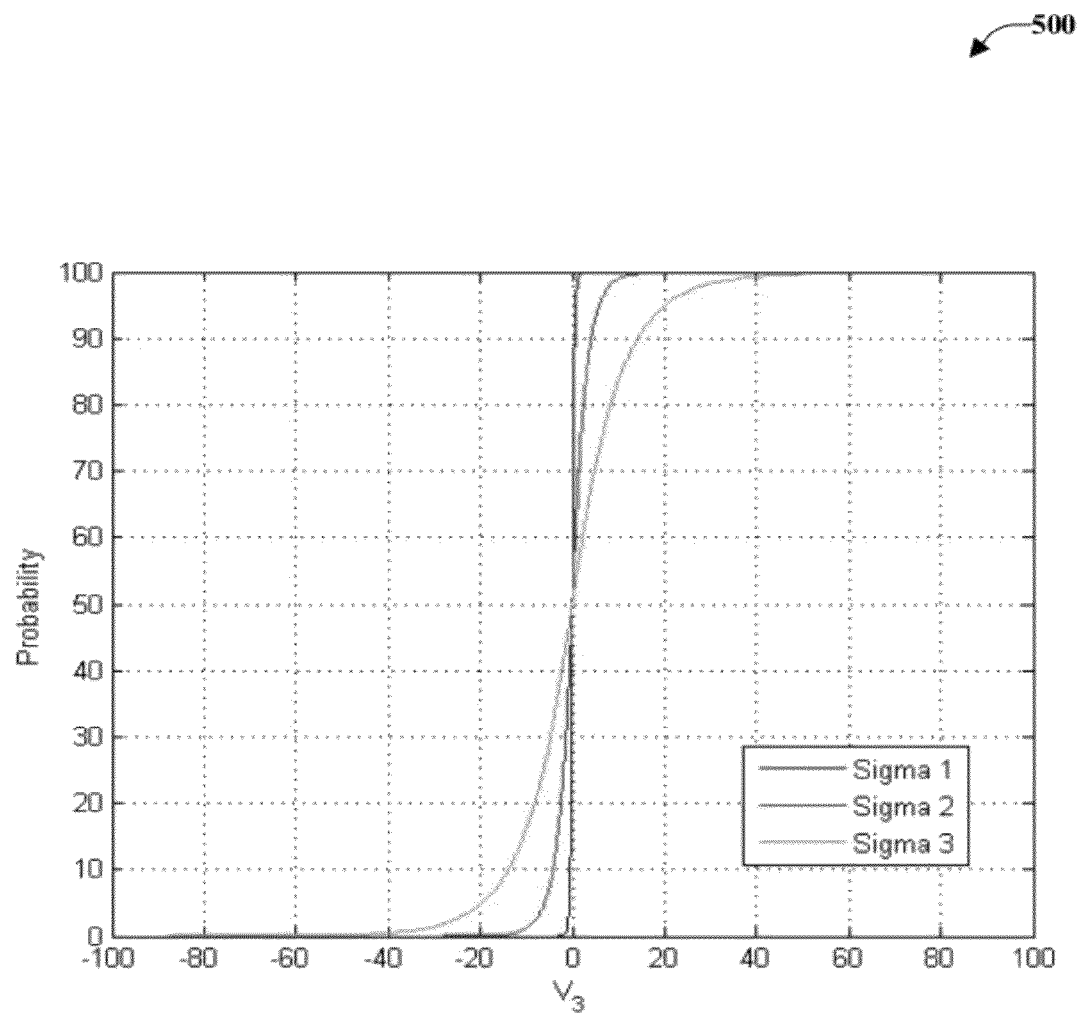
FIG. 5 is a plot of a cumulative probability function for the difference between an estimated third order moment and a theoretical third order moment ($V_3$) with twenty-five samples and a standard deviation of one, two, and three.

The standard deviation used with the determination of $V_3$ has an effect on the cumulative probability function. Referring now to FIG. 5, illustrated is a plot of the cumulative probability function for $V_3$ with twenty-five samples (N=25) and standard deviations of 1 (Sigma_1), 2 (Sigma_2) and 3 (Sigma_3). The shape of the cumulative probability function curve changes if the standard deviation is not 1. The $V_3$ cumulative probability function is roughly expanded by the standard deviation cubed.

Figure 6:
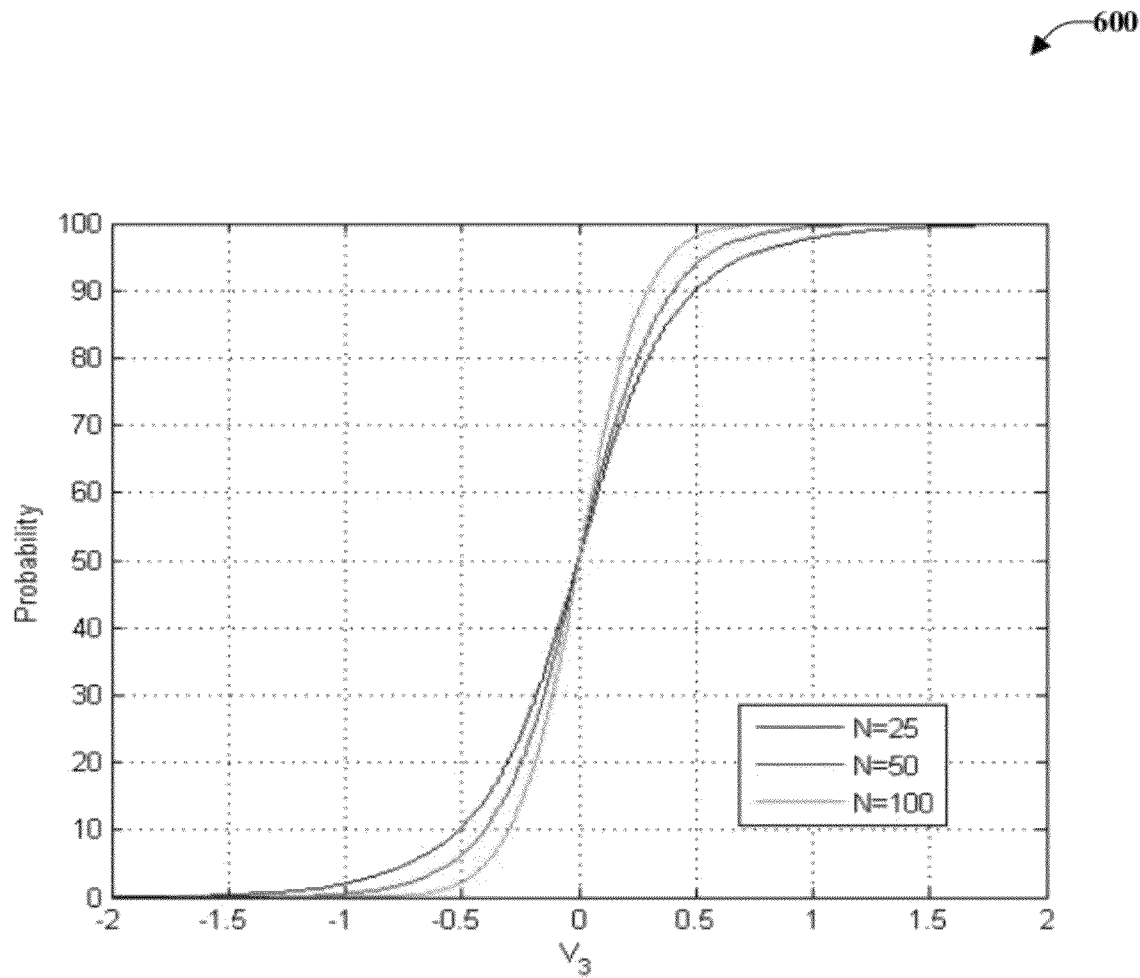
FIG. 6 is a plot a cumulative probability function for the difference between an estimated third order moment and a theoretical third order moment ($V_3$) with twenty-five, fifty and one-hundred samples and a standard deviation of one.

The number of samples (N) used for the determination of $V_3$ also has an effect on the cumulative probability function. Referring now to FIG. 6, illustrated is a plot 600 of the cumulative probability function for $V_3$ with twenty-five (N=25), fifty (N=50), and one-hundred (N=100) samples. As illustrated in plot 600, the number of samples (N) has a square root(N) type effect on straightening the curve. In practice, 25 samples were found to be a good number to achieve a fast no motion event with a low number of false motion events. Using a higher number of samples would be preferred if time were not a constraint.

Figure 7:
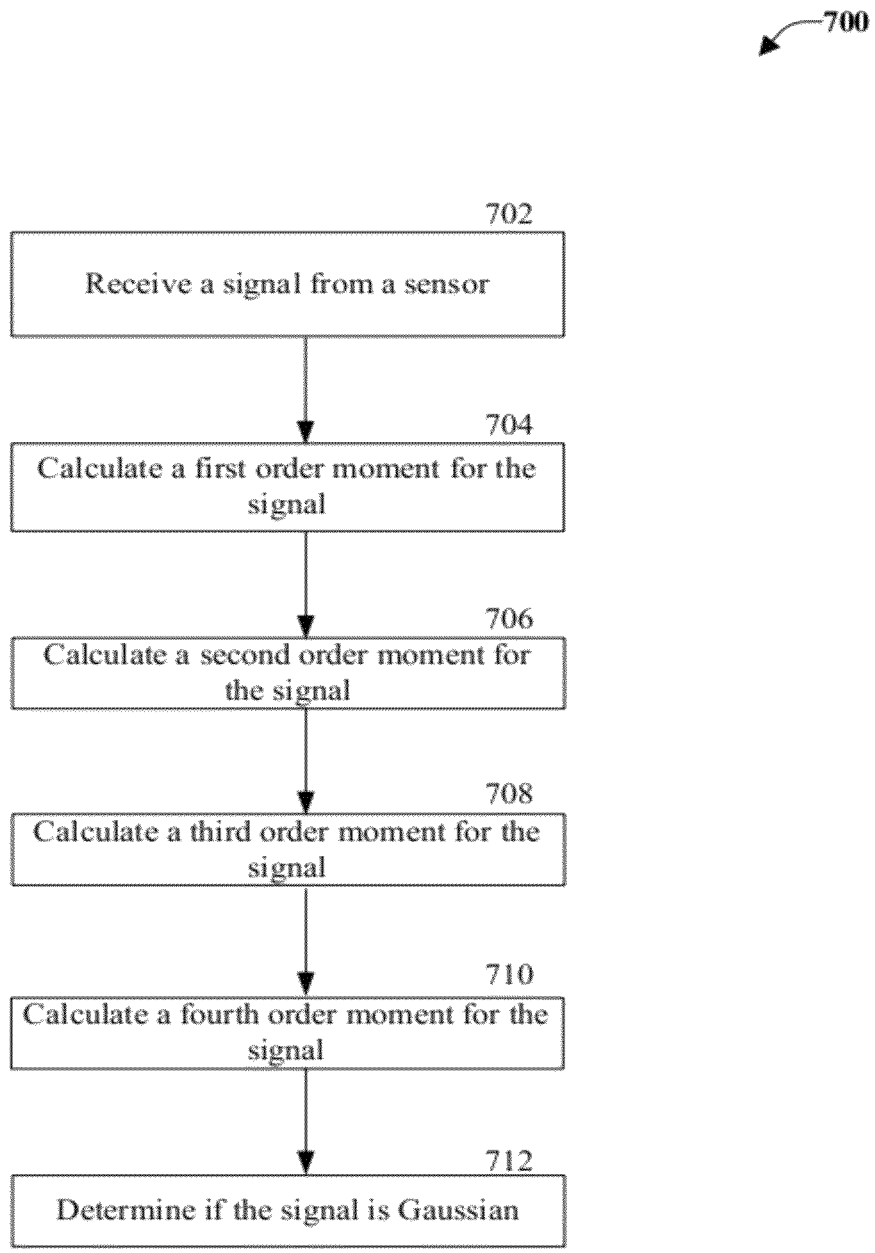
FIG. 7 is a schematic process flow diagram of a method for determining whether a signal is Gaussian.

One option to facilitate achieving a stricter requirement without a large time loss is shown in FIG. 7. Illustrated in FIG. 7 is a schematic process flow diagram of a method for determining whether a signal and/or data received from a sensor is Gaussian. As described above, if the signal and/or data are determined to be Gaussian, it can be determined that no motion event has occurred. In contrast, if the signal and/or data are determined to be non-Gaussian, it can be determined that a motion event has occurred.

At element 702, a signal can be received from a sensor (e.g., as described above). Similar to element 302 above, the signal can include data of size N. For example, the data can be $[x_0, x_1, \ldots, x_{N-1}]$. Additionally or alternatively, all axes of data from the sensor can be utilized (e.g., three axes). The processor can determine whether the data is Gaussian utilizing well defined moments.

At element 704, similar to element 304 above, the estimated first order moment for the data can be calculated. For example, the estimated first order moment ($T_1$) can be calculated according to the following:

$$T_1 = \frac{1}{N}\sum_{n=0}^{N-1}(x_n)^1,\qquad \text{EQUATION 1}$$

where $T_1$ is the estimated first order moment, N is the size of the data, and $x_n$ is a data point within $[x_0, x_1, \ldots, x_{N-1}]$.

At element 706, similar to element 306 above, the estimated second order moment for the data can be calculated. For example, the estimated second order moment ($T_2$) can be calculated according to the following:

$$T_2 = \frac{1}{N}\sum_{n=0}^{N-1}(x_n)^2,\qquad \text{EQUATION 2}$$

where $T_2$ is the estimated second order moment, N is the size of the data, and $x_n$ is a data point within $[x_0, x_1, \ldots, x_{N-1}]$.

At element 708, similar to element 308 above, the estimated third order moment for the data can be calculated. For example, the estimated third order moment ($T_3$) can be calculated according to the following:

$$T_3 = \frac{1}{N}\sum_{n=0}^{N-1}(x_n)^3,\qquad \text{EQUATION 3}$$

where $T_3$ is the estimated third order moment, N is the size of the data, and $x_n$ is a data point within $[x_0, x_1, \ldots, x_{N-1}]$.

To achieve a stricter requirement, at element 712, the estimated fourth order moment for the data can be calculated. For example, the estimated fourth order moment ($T_4$) can be calculated according to the following:

$$T_4 = \frac{1}{N}\sum_{n=0}^{N-1}(x_n)^4,\qquad \text{EQUATION 5}$$

where $T_4$ is the estimated fourth order moment, N is the size of the data, and $x_n$ is a data point within $[x_0, x_1, \ldots, x_{N-1}]$.

It is well known, that if a process is Gaussian, all third order and higher order moments (e.g., including the fourth order moment) can be calculated from the first order moment and the second order moment. At element 712, it can be determined if the signal is Gaussian by comparing the estimated fourth order moment calculated according to EQUATION 5 ($T_4$) to a theoretical fourth order Gaussian moment. The theoretical fourth order moment can be calculated based on the estimated first order moment ($T_1$) and the estimated second order moment ($T_2$). A difference ($V_4$) between the estimated fourth order moment ($T_4$) and the theoretical fourth order moment can be expressed as:

$$V_4 = T_4 - 3*T_2^2 + 2*T_1^4 - 4*V_3*T_1 \qquad \text{EQUATION 6,}$$

where $V_4$ is the difference between the estimated fourth order moment ($T_4$) and the theoretical fourth order moment based on estimated $T_1$, $T_2$ and $V_3$, $T_1$ is the estimated first order moment and $T_2$ is the estimated second order moment, and $V_3$ is found via EQUATION 4. $V_3$ may be non zero due to estimation errors.

In a Gaussian process, the fourth order moment $T_4$ should be equal to the moment computed by using the true first and second order moments. By using estimates of the moments and comparing the relationship when using estimates, the errors produced on the comparison should be small for a Gaussian process. For example, the absolute value of $V_4$ should be within a threshold range for the process to be Gaussian. Therefore, if the absolute value of $V_4$ is less than the threshold, the process is determined to be Gaussian, and the data from the sensor is determined to be due to a no motion event. In contrast, if the absolute value of $V_4$ is greater than the threshold, the process is determined to be non-Gaussian, and the data from the sensor is determined to be due to a motion event. The threshold may have to be increased if the sensor noise is not strictly Gaussian.

Figure 8:
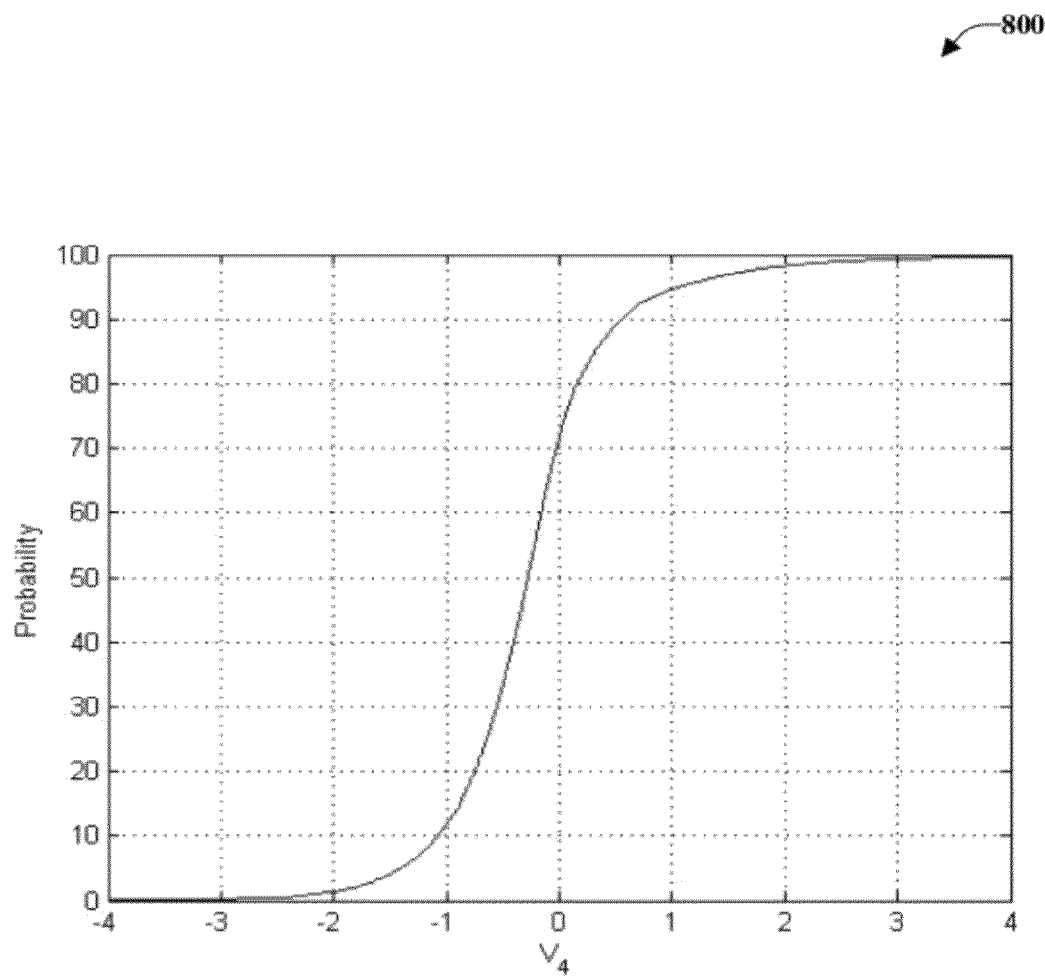
FIG. 8 is a plot of a cumulative probability function for the difference between an estimated fourth order moment and a theoretical fourth order moment ($V_4$).

$V_4$ can be computed according to EQUATION 6 for a known Gaussian sequence (e.g., $[x_1, x_2, \ldots, x_{N-1}]$ is known to be Gaussian) with a standard deviation of 1. Referring now to FIG. 8, illustrated is a plot 800 of a cumulative probability function for $V_3$ with twenty-five samples (N=25) and a standard deviation of 1. Given the plot 800, a probability of getting a no motion event can be set and a range that $V_4$ needs to be within to achieve the probability.

Figure 9:
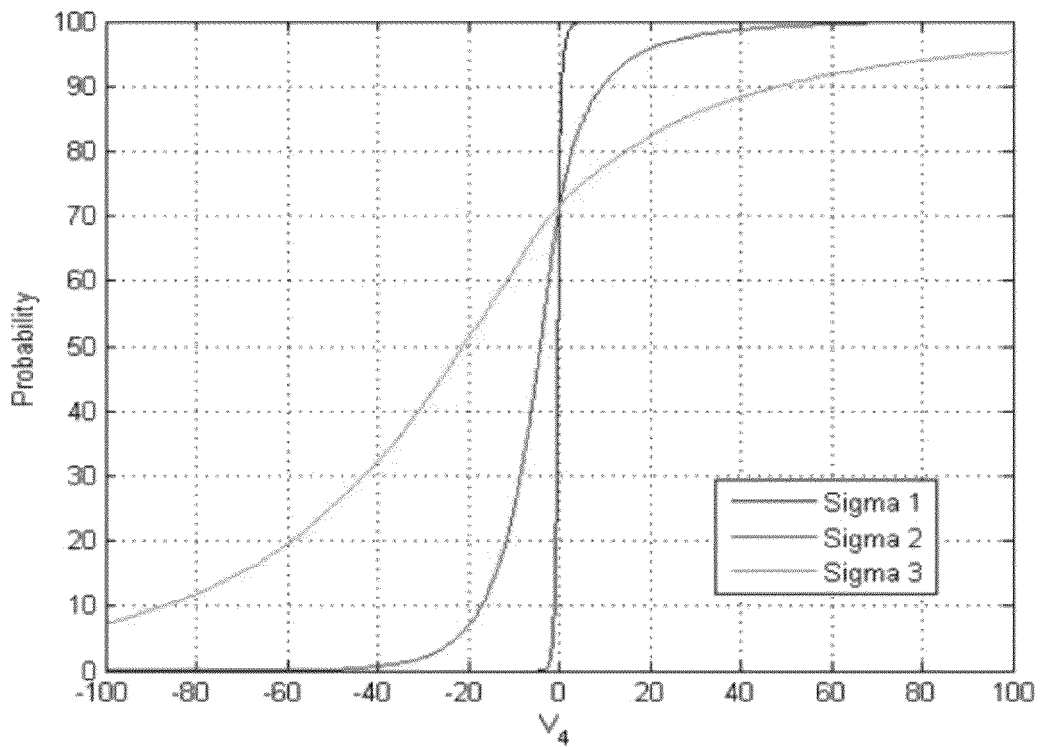
FIG. 9 is a plot of a cumulative probability function for the difference between an estimated fourth order moment and a theoretical fourth order moment ($V_4$) with twenty-five samples and a standard deviation of one, two, and three.

The standard deviation used with the determination of $V_4$ has an effect on the cumulative probability function. Referring now to FIG. 9, illustrated is a plot of the cumulative probability function for $V_4$ with twenty-five samples (N=25) and standard deviations of 1 (Sigma_1), 2 (Sigma_2) and 3

(Sigma_3). The shape of the cumulative probability function curve changes if the standard deviation is not 1. The $V_4$ cumulative probability function is roughly expanded by the standard deviation to the power of four.

Although not illustrated, the number of samples (N) used for the determination of $V_4$ also has an effect on the cumulative probability function. In practice, 25 samples are a good number to achieve fast no motion determinations with a low number of false motion events. Using a higher number of samples would be preferred if time were not a constraint.

Higher order moments can be utilized in the determination of a motion event or a no motion event. The same techniques as illustrated in FIGS. 3 and 7 can be extended to higher powers. However, the higher powers can add complexity and lose time benefits provided by the third or fourth order processes as illustrated in FIGS. 3 and 7. Additionally, the sensor (e.g., gyroscope) can exhibit non-Gaussian traits for higher order moments. However, by way of example, the fifth order difference can be found according to:

$$V_5 = T_5 - 15 * T_2^2 * T_1 + 20 * T_2 * T_1^3 - 6 * T_1^5 - 10 * V_3 * T_1^2 \quad \text{EQUATION 7,}$$

where $T_5$ is the estimated fifth order moment, $T_1$ is the estimated first order moment, $T_2$ is the estimated second order moment, and $V_3$ is found according to EQUATION 4.

By way of a non-limiting example, for more security in not getting a transition effect, more than a single motion event can be detected. For example, three motion events can be detected. The second or third motion event can be taken as the determination of a motion event or a no motion event. Since the number of samples is so few (e.g., N=25), the time to get the no motion event remains small.

Figure 10:
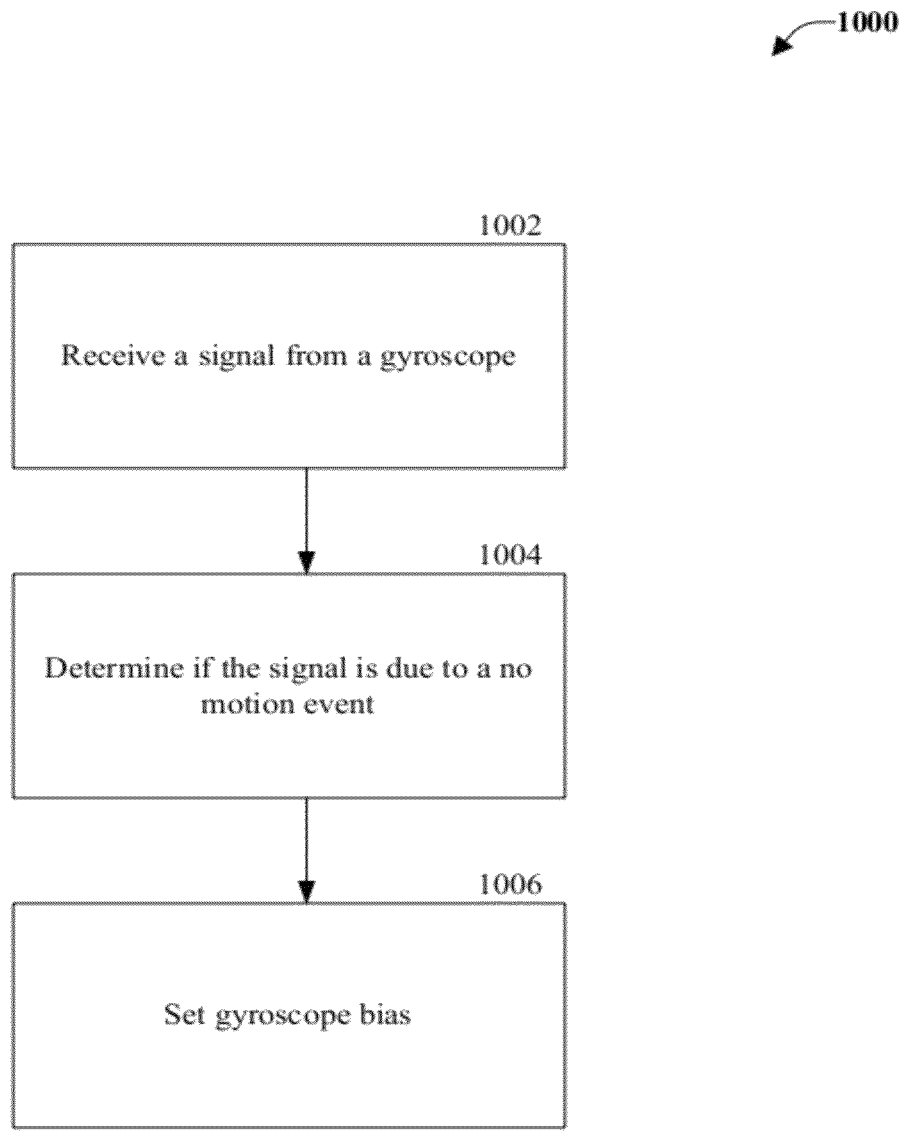
FIG. 10 is a schematic process flow diagram of a method for updating a bias of a gyroscope.

As a non-limiting example, the sensor can be a gyroscope and a determination of a no motion event can facilitate setting the bias of the gyroscope. Referring now to FIG. 10, illustrated is a schematic process flow diagram of a method for updating a bias of a gyroscope. At element 1002, a signal is received from a gyroscope. For example, the signal can include data of size N. For example, the data can be $[x_0, x_1, \ldots, x_{N-1}]$. Additionally or alternatively, all axes of gyroscope data can be utilized (e.g., three axes).

At element 1004, it can be determined (e.g., according to the methods illustrated in FIG. 3 or 7) that the signal is due to a no motion event. For example, the gyroscope data (e.g., $[x_0, x_1, \ldots, x_{N-1}]$) can be fed into the processes defined by FIG. 3 or FIG. 7. It can be determined according to FIG. 3 or FIG. 7 whether the data is due to a motion event or a no motion event. For example, if all values for each axes are within the proper threshold range, then a no motion event can be declared.

At element 1006, if the data is determined to be due to a no motion event, a bias of the gyroscope can be set. For example, the bias of the gyroscope can be set to the estimated first order moment ($T_1$). A gyroscope bias is easy to compute if it is known if the gyroscope is moving or not. On a typical gyroscope, the standard deviation is typically 1 or 2 bits, so just a few samples (e.g., N=25) would give a good estimate of bias upon a determination of whether the gyroscope is experiencing a motion event or a no motion event. The bias can simply be computed by taking an average of the gyroscope sensor data while the gyroscope is not moving (e.g., $T_1$).

In practice, a false motion event is of less concern than a false no motion event. This is because a false no motion event can cause the wrong gyro bias to be applied, whereas for a false motion event, no bias correction happens.

Figure 11:
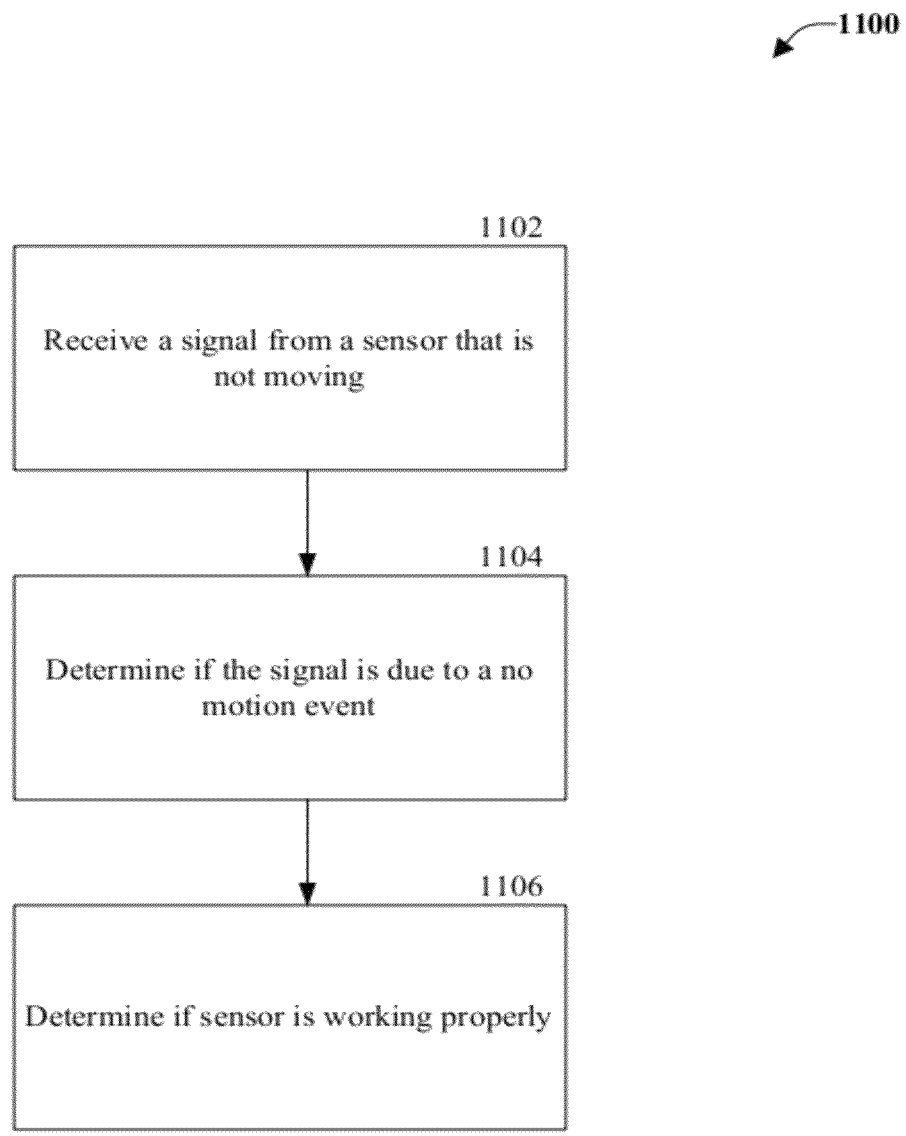
FIG. 11 is a schematic process flow diagram of a method for determining if a sensor is working properly.

If other sensors are attached, such as, an accelerometer, a compass, a pressure sensor, a proximity sensor, a range sensor, or the like, then that data can optionally also be run through the methods as illustrated in FIG. 3 and/or FIG. 7 and included in the motion event/no motion event determination. However, the bias for sensors other than the gyroscope cannot be determined according to the method as illustrated in FIG. 11.

According to another non-limited example, the methods as described in FIG. 3 and FIG. 7 can be applied during a test cycle to determine whether a sensor is good or not. Referring now to FIG. 11, illustrated is a schematic process flow diagram of a method for determining if a sensor is working properly.

At element 1102, a signal can be received from a sensor that is known to be experiencing a no motion event. For example, the signal can include data of size N. For example, the data can be $[x_0, x_1, \ldots, x_{N-1}]$. Additionally or alternatively, all axes of data from the sensor can be utilized (e.g., three axes).

At element 1104, it can be determined (e.g., according to the methods illustrated in FIG. 3 or 7) that the signal is due to a no motion event. For example, the data (e.g., $[x_0, x_1, \ldots, x_{N-1}]$) can be fed into the processes defined by FIG. 3 or FIG. 7. It can be determined according to FIG. 3 or FIG. 7 whether the data is due to a motion event or a no motion event. For example, if all values for each axes are within the proper threshold range, then a no motion event can be declared.

At element 1106, it can be determined whether the sensor is working properly. For example, at element 1102, the sensor is known to be experiencing a no motion event. If, at element 1104, it is determined that the sensor is experiencing a motion event, the sensor cannot be working properly. However, if, at element 1104, it is determined that the sensor is experiencing a no motion event, then the sensor, which is known to by experiencing a no motion event, is working properly.

If it is known that a device is not moving, $V_3$ as defined in FIG. 3 or $V_4$ as defined in FIG. 7 can be used to qualify a sensor as good or not in a test cycle. There is typically a small distribution of standard deviations for a particular sensor. If the standard deviation distribution is unknown, then the range of values accepted for a no motion event can be adjusted by multiplying the range of values by $(T_2 - T_1^2)^{3/2}$. It is still advisable to have a limit for the upper range that could be achieved for a no motion event.

Referring now to FIGS. 12-15, illustrated therein are exemplary computing networks 1200, computing environments 1300, and mobile devices 1400, 1500 that can facilitate implementation of the systems and methods described above. Each of figures 12-15 is not intended to be limiting, but, instead, to give a exemplary hardware context to the systems and methods described above.

Figure 12:
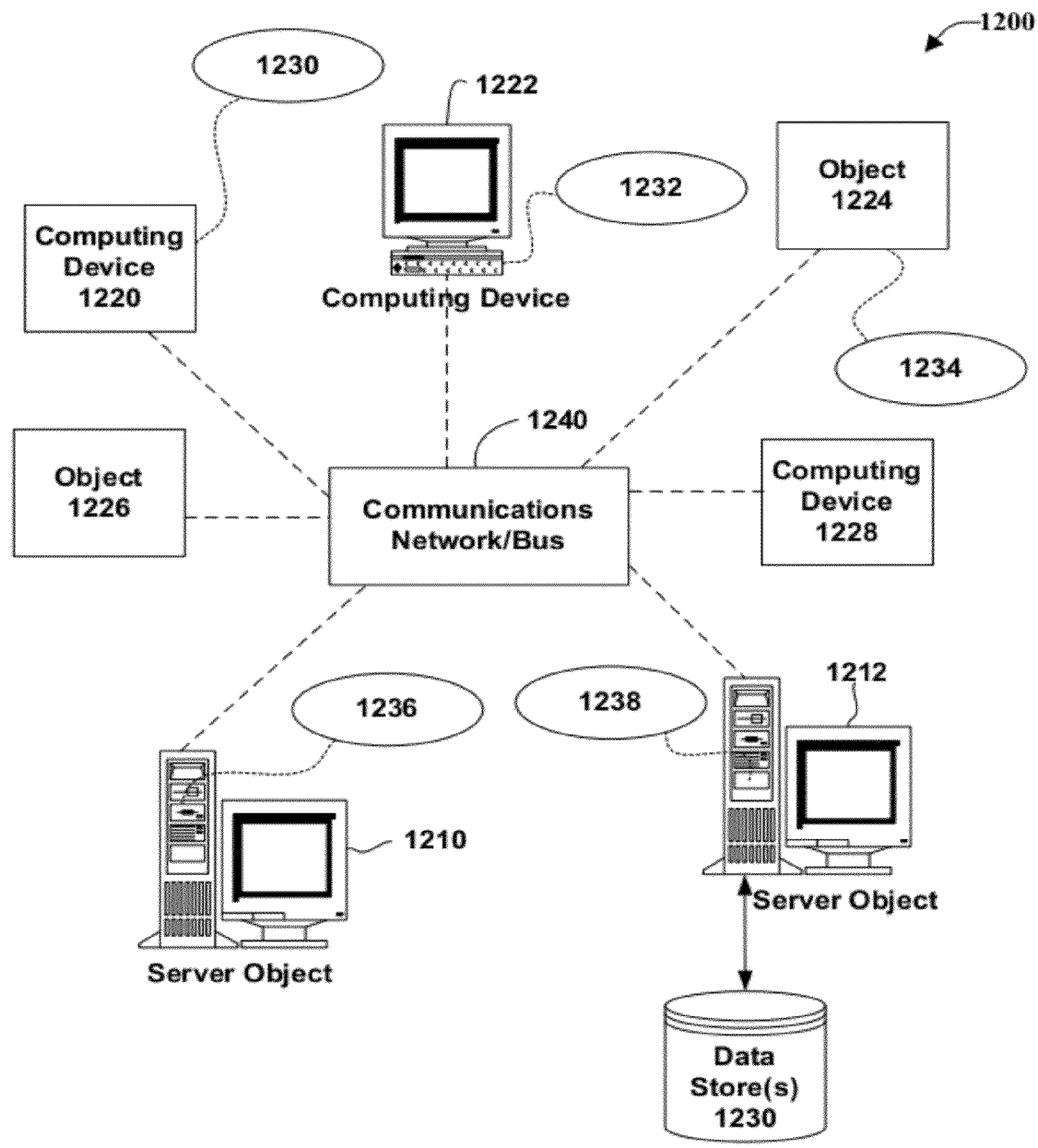
FIG. 12 illustrates an exemplary computer network in which various embodiments described herein can be implemented.

Referring now to FIG. 12, illustrated is a non-limiting schematic diagram of an exemplary networked or distributed computing environment 1200. The distributed computing environment comprises computing objects 1210, 1212, etc. and computing objects or devices 1220, 1222, 1224, 1226, 1228, etc., which can include programs, methods, data stores, programmable logic, etc., as represented by applications 1230, 1232, 1234, 1236, 1238. It can be appreciated that objects 1210, 1212, etc. and computing objects or devices 1220, 1222, 1224, 1226, 1228, etc. can comprise different devices, such as remote controllers, PDAs, audio/video devices, mobile phones, MP3 players, laptops, etc.

Each object 1210, 1212, etc. and computing objects or devices 1220, 1222, 1224, 1226, 1228, etc. can communicate with one or more other objects 1210, 1212, etc. and computing objects or devices 1220, 1222, 1224, 1226, 1228, etc. by way of the communications network 1240, either directly or indirectly. Even though illustrated as a single element in FIG. 12, network 1240 can comprise other computing objects and computing devices that provide services to the system of FIG. 12, and/or can represent multiple interconnected networks, which are not shown. Each object 1210, 1212, etc. or 1220, 1222, 1224, 1226, 1228, etc. can also contain an application, such as applications 1230, 1232, 1234, 1236, 1238, that might make use of an API, or other object, software, firmware and/or hardware, suitable for communication with or implementation of the delayed interaction model as provided in accordance with various embodiments.

There are a variety of systems, components, and network configurations that support distributed computing environments. For example, computing systems can be connected together by wired or wireless systems, by local networks or widely distributed networks. Currently, many networks are coupled to the Internet, which provides an infrastructure for widely distributed computing and encompasses many different networks, though any network infrastructure can be used for exemplary communications made incident to the techniques as described in various embodiments.

Thus, a host of network topologies and network infrastructures, such as client/server, peer-to-peer, or hybrid architectures, can be utilized. In a client/server architecture, particularly a networked system, a client is usually a computer that accesses shared network resources provided by another computer, e.g., a server. In the illustration of FIG. 12, as a non-limiting example, computers 1220, 1222, 1224, 1226, 1228, etc. can be thought of as clients and computers 1210, 1212, etc. can be thought of as servers where servers 1210, 1212, etc. provide data services, such as receiving data from client computers 1220, 1222, 1224, 1226, 1228, etc., storing of data, processing of data, transmitting data to client computers 1220, 1222, 1224, 1226, 1228, etc., although any computer can be considered a client, a server, or both, depending on the circumstances. Any of these computing devices can be processing data, or requesting services or tasks that can implicate the delayed interaction model and related techniques as described herein for one or more embodiments.

A server is typically a remote computer system accessible over a remote or local network, such as the Internet or wireless network infrastructures. The client process can be active in a first computer system, and the server process can be active in a second computer system, communicating with one another over a communications medium, thus providing distributed functionality and allowing multiple clients to take advantage of the information-gathering capabilities of the server. Any software objects utilized pursuant to the direction based services can be provided standalone, or distributed across multiple computing devices or objects.

In a network environment in which the communications network/bus 1240 is the Internet, for example, the servers 1210, 1212, etc. can be Web servers with which the clients 1220, 1222, 1224, 1226, 1228, etc. communicate via any of a number of known protocols, such as the hypertext transfer protocol (HTTP). Servers 1210, 1212, etc. can also serve as clients 1220, 1222, 1224, 1226, 1228, etc., as can be characteristic of a distributed computing environment.

As a further non-limiting example, various embodiments described herein apply to any handheld, portable and other computing devices and computing objects of all kinds are contemplated for use in connection with the various embodiments described herein, i.e., anywhere that a device can request pointing based services. Accordingly, the general purpose remote computer described below in FIG. 3 is but one example, and the embodiments of the subject disclosure can be implemented with any client having network/bus interoperability and interaction.

Although not required, any of the embodiments can partly be implemented via an operating system, for use by a developer of services for a device or object, and/or included within application software that operates in connection with the operable component(s). Software can be described in the general context of computer executable instructions, such as program modules, being executed by one or more computers, such as client workstations, servers or other devices. Those skilled in the art will appreciate that network interactions can be practiced with a variety of computer system configurations and protocols.

Figure 13:
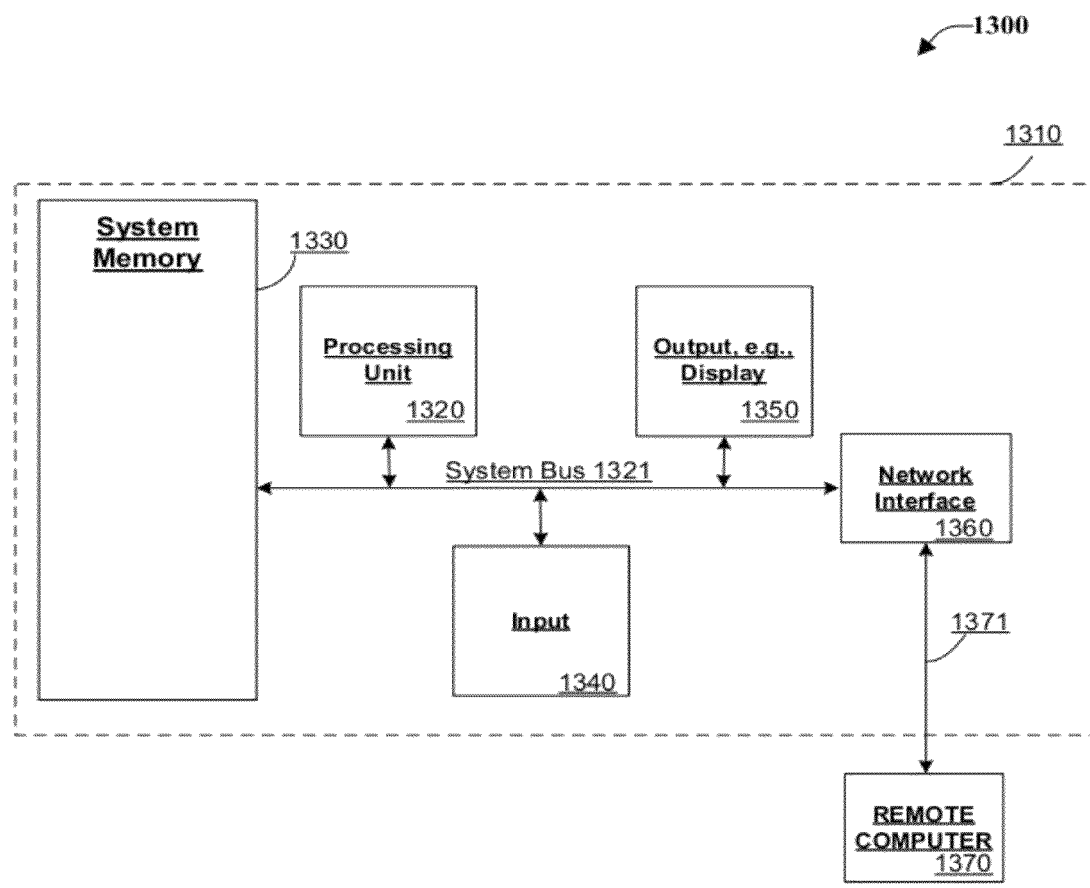
FIG. 13 illustrates an exemplary computing environment in which the various embodiments described herein can be implemented.

FIG. 13 illustrates an example of a suitable computing system environment 1300 in which one or more of the embodiments can be implemented, although as made clear above, the computing system environment 1300 is only one example of a suitable computing environment and is not intended to suggest any limitation as to the scope of use or functionality of any of the embodiments. Neither should the computing environment 1300 be interpreted as having any dependency or requirement relating to any one or combination of components illustrated in the exemplary operating environment 1300.

With reference to FIG. 13, an exemplary remote device for implementing one or more embodiments herein can include a general purpose computing device in the form of a handheld computer 1310. Components of handheld computer 1310 can include, but are not limited to, a processing unit 1320, a system memory 1330, and a system bus 1321 that couples various system components including the system memory to the processing unit 1320.

Computer 1310 typically includes a variety of computer readable media and can be any available media that can be accessed by computer 1310. The system memory 1330 can include computer storage media in the form of volatile and/or nonvolatile memory such as read only memory (ROM) and/or random access memory (RAM). By way of example, and not limitation, memory 1330 can also include an operating system, application programs, other program modules, and program data.

A user can enter commands and information into the computer 1310 through input devices 1340. A monitor or other type of display device is also connected to the system bus 1321 via an interface, such as output interface 1350. In addition to a monitor, computers can also include other peripheral output devices such as speakers and a printer, which can be connected through output interface 1350.

The computer 1310 can operate in a networked or distributed environment using logical connections to one or more other remote computers, such as remote computer 1370. The remote computer 1370 can be a personal computer, a server, a router, a network PC, a peer device or other common network node, or any other remote media consumption or transmission device, and can include any or all of the elements described above relative to the computer 1310. The logical connections depicted in FIG. 13 include a network 1371, such local area network (LAN) or a wide area network (WAN), but can also include other networks/buses. Such networking environments are commonplace in homes, offices, enterprise-wide computer networks, intranets and the Internet.

Figure 14:
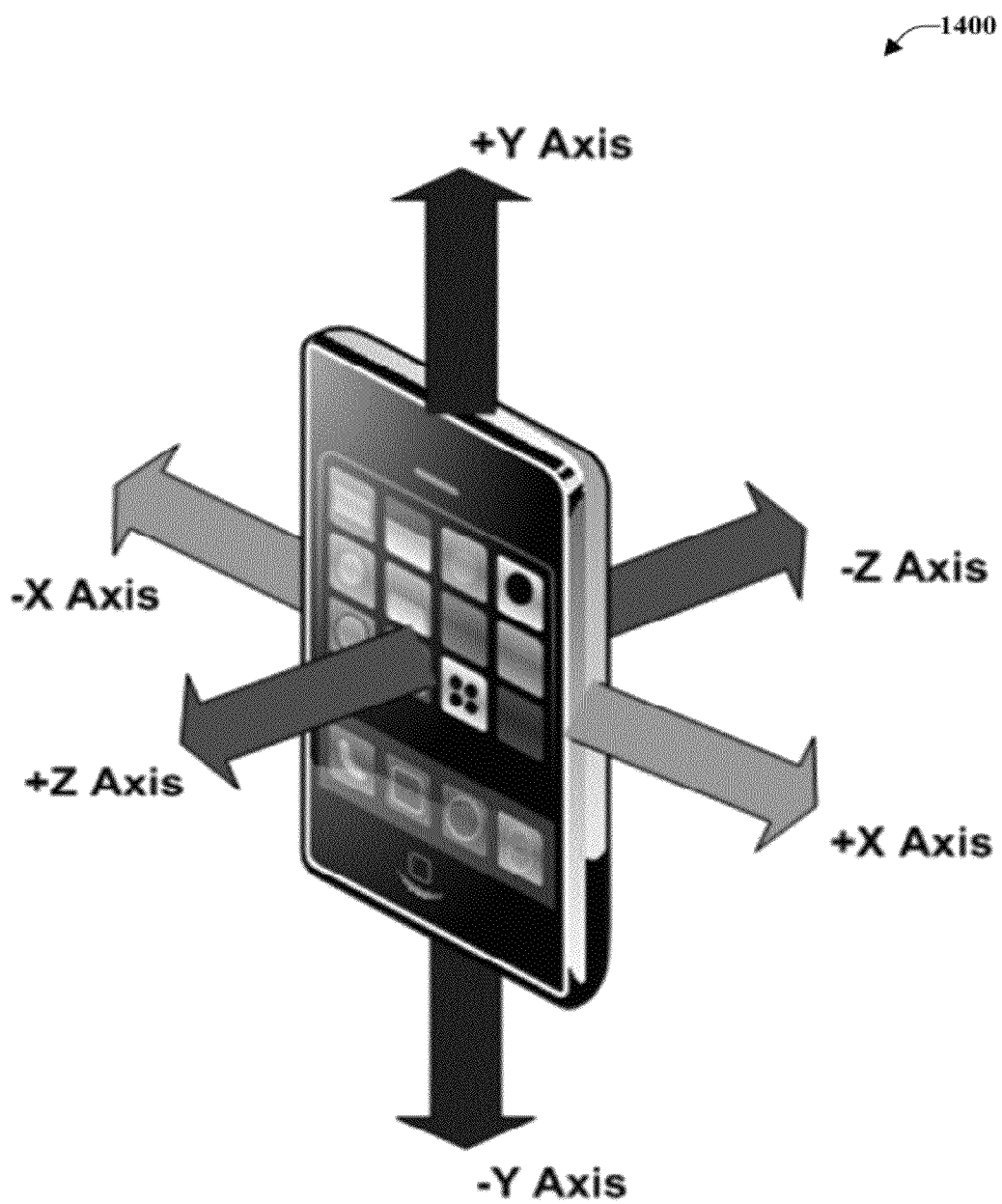
FIG. 14 illustrates an exemplary handheld device in which various embodiments described herein can be implemented.
Figure 15:
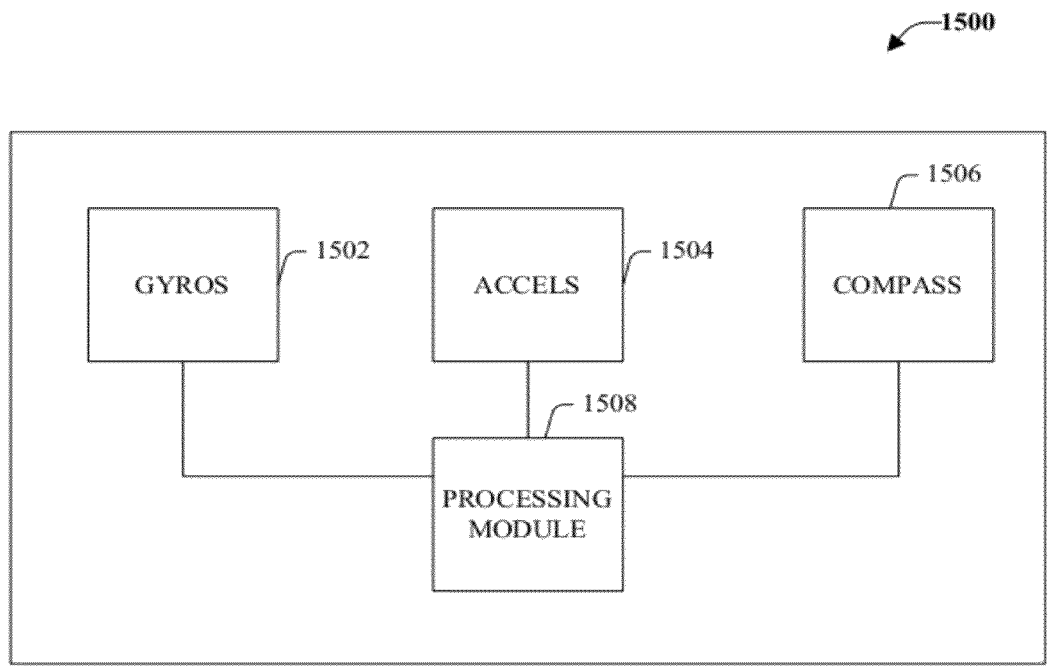
FIG. 15 illustrates an exemplary handheld device in which various embodiments described herein can be implemented.

As described above, various embodiments can be embodied on a mobile device. FIGS. 14 and 15 illustrate exemplary embodiments of a mobile device. Referring now to FIG. 14, illustrated is a mobile device 1400 that can be moved in on three axes. As illustrated in FIG. 15, the mobile device 1500 can include sensors, such as a gyroscope 1502, an accelerometer 1504, and/or a compass 1506 (the mobile device can also any sensor that can sense inertia, pressure, proximity, range, and the like, although it is not illustrated; the gyroscope 1502, accelerometer 1504, and compass 1506 are merely exemplary). The sensors can be communicatively coupled to a processing module 1508. For example, one or more sensors can be on an IC chip, as described above (e.g., sensor chip 102). The sensor chip can have associated processing power and/or capabilities. Additionally, processing module 1508 can have additional processing power and/or capabilities (e.g., host device 104). The sensors 1502-1506 as illustrated in FIG. 15 can experience motion on three axes as illustrated in FIG. 14. Data from the sensors on the three axes can be fed into the methods as illustrated in FIG. 3 and FIG. 7 and the motion/no motion determination made based on the data from the three axes.

While the various embodiments have been described in connection with the various figures, it is to be understood that other similar embodiments can be used or modifications and additions can be made to the described embodiment for performing the same function without deviating therefrom. Therefore, the present innovation should not be limited to any single embodiment, but rather should be construed in breadth and scope in accordance with the appended claims.

What is claimed is:

1. A computer implemented method, comprising:
receiving a data signal from a motion sensor, wherein the data signal comprises data values as a function of user motion and noise; wherein a computer executes instructions for:
determining an average of the data values; wherein the average of the data values comprises a first order moment;
determining an average of squares of the data values; wherein the average of the squares of the data values comprises a second order moment;
determining an average of cubes of the data values;
determining a difference between a third order moment calculated only using the average of cubes and a third order moment calculated using only the first and second order moments; and
determining whether a user motion event has occurred based on the difference.

2. The computer implemented method of claim 1, wherein the determining further comprises determining that no user motion has occurred when the difference is within a threshold range.

3. The computer implemented method of claim 2, wherein the receiving the data signal comprises receiving the data signal from an accelerometer.

4. The computer implemented method of claim 2, wherein the receiving the data signal comprises receiving the data signal from a compass.

5. The computer implemented method of claim 2, wherein the receiving the data comprises receiving the data from a gyroscope.

6. The computer implemented method of claim 5, further comprising setting a gyroscope bias when no user motion has occurred.

7. The computer implemented method of claim 5, wherein the setting further comprises setting the gyroscope bias to the average of the data values.

8. The computer implemented method of claim 5, wherein the determining further comprising setting a gyroscope temperature compensation learning term when no user motion has occurred.

9. The computer implemented method of claim 1, wherein the noise is Gaussian noise.

10. The computer implemented method of claim 1, further comprising:
determining an average of fourth powers of the data values;
determining a second difference between the average of the fourth powers and an expected fourth order moment, wherein the expected fourth order moment is calculated from the average of the squares and the average of the data values; and
determining whether a user motion event has occurred based on the second difference.

11. The computer implemented method of claim 1, further comprising:
determining an average of fourth powers of the data values;
determining an average of fifth powers of the data values;
determining a third difference between the average of the fifth powers and an expected fifth order moment, wherein the expected fifth order moment is calculated from the from the average of the squares and the average of the data values; and
determining whether a user motion event has occurred based on the third difference.

12. A computer implemented method, comprising:
receiving a data signal from a motion sensor, wherein the data signal comprises data values as a function of motion and noise, when the motion sensor is known not to be moving;
wherein a computer executes instructions for:
determining an average of the data values; wherein the average of the data values comprises a first order moment;
determining an average of squares of the data values; wherein the average of the squares of the data values comprises a second order moment
determining an average of cubes of the data values;
determining a difference between a third order moment calculated only using the average of cubes and a third order moment calculated using only the first and second order moments; and
determining whether the motion sensor is working properly based on the difference.

13. The computer implemented method of claim 12, wherein the determining whether the motion sensor is working properly further comprising confirming that the motion sensor has recorded a no motion event if the difference is within a threshold range.

14. The computer implemented method of claim 12, wherein the receiving the data signal further comprises receiving the data signal from an accelerometer.

15. The computer implemented method of claim 12, wherein the receiving the data signal further comprises receiving the data signal from a compass.

16. The computer implemented method of claim 12, wherein the receiving the data signal further comprises receiving the data signal from a gyroscope.

17. The computer implemented method of claim 12, further comprising:
determining an average of fourth powers of the data values;
determining a second difference between the average of the fourth powers and an expected fourth order moment, wherein the expected fourth order moment is calculated from the average of the squares and the average of the data values; and
determining whether the motion sensor is working properly based on the second difference.

18. A system, comprising:
- a sensor chip comprising a gyroscope and a first processor configured to run a motion detection algorithm on data from the gyroscope;
- a host device communicatively coupled to the sensor chip comprising a second processor configured to independently run the motion detection algorithm on the data from the sensor chip and further configured to run a temperature compensation algorithm, wherein the data signal comprises data values as a function of user motion and noise; wherein the motion detection algorithm determines an average of the data values; wherein the average of the data values comprises a first order moment; determines an average of squares of the data values; wherein the average of the squares of the data values comprises a second order moment; determines an average of cubes of the data values; determines a difference between a third order moment calculated only using the average of cubes and a third order moment calculated using only the first and second order moments; and determines whether a user motion event has occurred based on the difference;
- wherein when the motion detection algorithm running on the first processor detects a no motion event, the second processor records a bias for the gyroscope that is used within the temperature compensation algorithm.

19. The system of claim 18, wherein the host device is communicatively coupled to the sensor chip via an I2C bus or a serial port.

20. The system of claim 18, wherein the host device utilizes the data from the gyroscope to feed the motion detection algorithm.

21. The system of claim 18, wherein the first processor is configured to determine that no motion has occurred upon an end of a time period or a temperature change and to utilize the bias for the gyroscope.

22. The system of claim 18, wherein the second processor is configured to run the motion detection algorithm in parallel with the first processor.

23. A computer implemented method, comprising:
- receiving a data signal from a motion sensor, wherein the data signal comprises data values as a function of user motion and noise; wherein a computer executes instructions for:
- determining an average of the data values; wherein the average of the data values comprises a first order moment;
- determining an average of squares of the data values; wherein the average of the squares of the data values comprises a second order moment;
- determining an average of cubes of the data values;
- determining a difference based on the equation $$V_3 = T_3 - (3 \ast T_2 \ast T_1 - 2 \ast T_1^3),$$

where $V_3$ is the difference between the estimated third order moment ($T_3$) and the theoretical third order moment based on $T_1$ and $T_2$, $T_1$ is the estimated first order moment and $T_2$ is the estimated second order moment; and
- determining whether a user motion event has occurred based on the difference.

24. The computer implemented method of claim 23 further includes:
- determining an average of fourth power of the data values;
- determining a difference based on the equation $$V_4 = T_4 - (3 \ast T_2^2 - 2 \ast T_1^4 + 4 \ast V_3 \ast T_1),$$

where $V_4$ is the difference between the estimated fourth order moment ($T_4$) and the theoretical fourth order moment based on estimated $T_1$, $T_2$ and $V_3$, and
- determining whether a user motion event has occurred based on the difference.

* * * * *